(12) United States Patent
Salisbury et al.

(10) Patent No.: US 9,382,568 B2
(45) Date of Patent: Jul. 5, 2016

(54) DETERMINING THE SENSITIVITY OF A CELL TO A DRUG

(75) Inventors: Vyvyan Clare Salisbury, Bristol (GB); Habib Mahmoud Alloush, Bristol (GB); Margaret Ann Smith, Bristol (GB); Paul John Innocenzi, Crumlin (GB); Mark William Ruddock, Crumlin (GB); Ashley Diane Martin, Crumlin (GB)

(73) Assignees: RANDOX LABORATORIES LTD. (GB); UNIVERSITY OF THE WEST OF ENGLAND, Bristol (GB)

( * ) Notice: Subject to any disclaimer, the term of this patent is extended or adjusted under 35 U.S.C. 154(b) by 562 days.

(21) Appl. No.: 13/058,035

(22) PCT Filed: Aug. 10, 2009

(86) PCT No.: PCT/GB2009/001969
§ 371 (c)(1),
(2), (4) Date: Apr. 14, 2011

(87) PCT Pub. No.: WO2010/015844
PCT Pub. Date: Feb. 11, 2010

(65) Prior Publication Data
US 2011/0183317 A1 Jul. 28, 2011

(30) Foreign Application Priority Data
Aug. 8, 2008 (GB) .................................. 0814591.4

(51) Int. Cl.
*C12Q 1/06* (2006.01)
*C12Q 1/66* (2006.01)
(Continued)

(52) U.S. Cl.
CPC ...................................... *C12Q 1/025* (2013.01)

(58) Field of Classification Search
CPC .............. C12Q 1/00; C12Q 1/02; C12Q 1/04; C12Q 1/025; C12Q 2563/103; C12Q 2563/107; C12Q 2565/00; C12Q 2565/20; C12Q 2565/301; G01N 1/6428; G01N 33/582
See application file for complete search history.

(56) References Cited

FOREIGN PATENT DOCUMENTS

WO  WO 94/28169   * 12/1994  ............... C12Q 1/66
WO  WO 2010/015844  2/2010

OTHER PUBLICATIONS

Smith et al. Blood. V2005. vol. 106(11). PArt 1, p. 695A.*
(Continued)

*Primary Examiner* — J. Hines
(74) *Attorney, Agent, or Firm* — Saliwanchik Lloyd & Eisenschenk

(57) ABSTRACT

The present invention provides an in vitro method for determining the resistance or sensitivity of a cell line or patient sample to a deoxyribonucleoside kinase-dependent drug, wherein the method comprises the steps of: (i) treating a patient sample or cell line, or a portion thereof, with a deoxyribonucleoside kinase-dependent drug; (ii) lysing the cells of the patient sample or cell line from step (i); (iii) optionally, mixing a portion of the cell lysate from step (ii) with a bioluminescent reporter bacteria incorporating a gene coding for deoxyribonucleoside kinase; (iv) mixing a portion of the cell lysate from (ii) with a bioluminescent reporter bacteria incorporating a gene coding for a deoxyribonucleoside kinase and a deoxyribonucleoside kinase transcription promoter; (v) mixing a portion of the cell lysate from step (ii) with a bioluminescent reporter bacteria incorporating a gene coding for a deoxyribonucleoside kinase, a deoxyribonucleoside kinase transcription promoter and a dephosphorylating agent; and (vi) measuring the bioluminescence of each of the mixtures from steps (iii) to (v), wherein the comparative levels of bioluminescence of each of the mixtures provides a measure of the resistance or sensitivity to the drug.

15 Claims, 7 Drawing Sheets

(51) Int. Cl.
   *C12Q 1/70*      (2006.01)
   *G01N 33/53*     (2006.01)
   *G01N 33/573*    (2006.01)
   *C12Q 1/02*      (2006.01)

(56) References Cited

OTHER PUBLICATIONS

Smith et al., (Blood ASH Annual Meeting Abstracts 2005 vol. 106 Abstract 2473).*

Sun Z-Q et al., "Expression of Cytidine Deaminase mRNA in Bone Marrow Cells from Patients with Acute Leukemia" *Journal of Experimental Hematology / Chinese Association of Pathophysiology*, 2003, 11(3):246-250.

Alloush HM et al., "Construction of a novel bioluminescence bacterial biosensor for real-time monitoring of cytotoxic drugs activity" *Luminescence*, 2004, 19:131. [Abstract].

Alloush HM et al., "Evaluation of a bioluminescent bacterial biosensor for rapid assay of cytotoxic drug activity in cell lines and clinical samples from leukaemic patients" *Luminescence*, 2006, 21:269-298. [Abstract].

Lamont JV et al., "A novel bioluminescent bacterial biosensor for the rapid pre-screening of chemotherapy efficacy" *Clinical Chemistry*, 2009, 55(6), Supplement. [Abstract No. A-117, p. A38].

Smith et al., "A Rapid Assay of Cytosine Arabinoside Uptake and Metabolism by Acute Myeloid Leukaemic Cells Using a Bioluminescent Bacterial Biosensor" *Blood*, (AAH Annual Meeting Abstracts), 2007, 110, Abstract 4308.

Wang et al., "An *Escherichia coli* System Expressing Human Deoxyribonucleoside Salvage Enzymes for Evaluation of Potential Antiproliferative Nucleoside Analogs" *Antimicrobial Agents and Chemotherapy*, 1998, 42(10):2620-2625.

International Search Report issued Feb. 12, 2009, in International Application No. PCT/GB2009/001969.

International Preliminary Report on Patentability issued Jul. 9, 2010, in International Application No. PCT/GB2009/001969.

Smith et al., "Development of a novel assay using bioluminescent reporter bacteria to determine the sensitivity of AML cells to cytosine arabinoside" *Blood*, 2005, 106(11), Part 1, p. 695A.

Sun ZQ et al., "Expression of cytidine deaminase mRNA in bone marrow cells from patients with acute leukemia" *Zhongguo Shi Yan Xue Ye Xue Za Zhi*, 2003, 11(3):246-250 (Abstract only).

Winzer K et al., "LuxS: its role in central metabolism and the in vitro synthesis of 4-hydroxy-5-methyl-3(2H)-furanone" *Microbiology*, 2002, 148:909-922.

* cited by examiner

DETERMINING THE SENSITIVITY OF A CELL TO A DRUG

FIELD OF THE INVENTION

The present invention relates to methods and kits for determining the sensitivity of cells to nucleoside analogue drugs.

BACKGROUND OF THE INVENTION

Acute myeloid leukaemia (AML) is a term used to define a heterogeneous group of haematological disorders resulting from the malignant transformation of myeloid precursor cells. Transformation leads to the proliferation of immature and undifferentiated cells in the blood and bone marrow and suppression of normal haemopoiesis. Effective treatment of AML patients is challenging and the clinical outcome can be disappointing and unpredictable. Only 70% of newly diagnosed patients receiving standard regimens respond to treatment. Furthermore, a large proportion of these patients fail to achieve long-term remission and develop resistance to subsequent therapy.

Nucleoside analogues (NA) are a class of antimetabolite drug widely used in the treatment of certain types of cancer and viral infections. These compounds resemble structurally the body's natural nucleosides and are subject to the same physiological uptake and metabolic mechanisms which results in their incorporation into newly synthesised DNA. This DNA-adulteration results in DNA synthesis inhibition and chain termination leading to cell death. NA are prodrugs that require phosphorylation into triphosphates to form the active nucleotide. Certain NA do not disrupt directly DNA replication. For example, the anti-herpes drug acyclovir, following cellular uptake and phosphorylation, disrupts DNA replication by inhibiting DNA polymerase.

The nucleoside analogue Ara-C is one of the most active single anti-cancer agents and has been the mainstay treatment of AML for over three decades. In vivo, Ara-C is transported into the cell via the specific nucleoside transporter hENT1 and is rapidly phosphorylated by dCK to its monophosphate form. Ara-CMP is further phosphorylated by nucleoside kinases into its active tri-phosphorylated form, Ara-CTP. The anti-proliferative and cytotoxic effects of Ara-CTP are due to its ability to interfere with DNA polymerase and to incorporate into DNA strands leading to chain termination and arrest of DNA synthesis. High-dose Ara-C can also cause accumulation of cytochrome C in the cytosol, loss of mitochondrial membrane potential and increase in the reactive oxygen species.

Chemoresistance to Ara-C can arise from a number of factors influencing the rate of Ara-CTP formation and incorporation into DNA, including low drug uptake, conversion into Ara-U by cytidine deaminase, or dephosphorylation of the active metabolite by cytoplasmic nucleotidases.

The primary mechanism of resistance to nucleoside analogue drugs is due to insufficient NA triphosphate. The main causes of this are decreased levels of phosphorylating enzymes (e.g. dCK), inefficient cellular uptake (e.g. decreased levels of hENT1), increased levels of NA degrading enzymes (notably cytidine deaminase, cdd), and expansion of deoxyribonucleotide triphosphate (dNTP) pools. Deoxyribonucleoside kinase (dNK) levels are also considered to play key a role in drug resistance.

Ara-C has no effect on *Escherichia coli* as it lacks dCK and deaminates Ara-C into Ara-uracil through the activity of deoxycytidine deaminase (cdd). Wang et al., *Antimicrob. Agents. Chemother.*, 1998, 42:2620-2625, described the construction of a cdd-deficient *E. coli* mutant (SØ5218) which, upon the expression of human dCK gene, exhibited reduced relative growth in the presence of Ara-C. The Ara-C effect on growth was completely abolished when assayed in the absence of the dCK inducible promoter, IPTG, indicating human dCK expression in the bacteria leads to Ara-CTP incorporation into bacterial DNA.

In vitro assessment of Ara-C efficacy has traditionally involved measurement of a) cell death b) reduction in S phase activity or c) use of AML clonogenic assays following exposure of leukaemic cells to Ara-C. These methods are non-standardised, time-consuming, expensive and are not suitable for routine screening. Therefore, patients are treated with regimens including Ara-C regardless of their sensitivity to the drug and can suffer debilitating side-effects such as myelosuppression, nausea, diarrhoea, vomiting and the development of drug-resistant secondary cancers.

Thus there is a need for a simple, rapid pre-screening test for determining nucleoside analogue drug efficacy in patients.

SUMMARY OF THE INVENTION

The present invention is directed to methods and kits for determining the resistance or sensitivity of cells to deoxyribonucleoside kinase-dependent drugs.

According to a first aspect of the invention, an in vitro method for determining the resistance or sensitivity of a cell line or patient sample to a deoxyribonucleoside kinase-dependent drug comprises the steps of:
  (i) treating a patient sample or cell line, or a portion thereof, with a deoxyribonucleoside kinase-dependent drug;
  (ii) lysing the cells of the patient sample or cell line from step (i);
  (iii) mixing a portion of the cell lysate from (ii) with a bioluminescent reporter bacteria incorporating a gene coding for a deoxyribonucleoside kinase and a deoxyribonucleoside kinase transcription promoter;
  (iv) mixing a portion of the cell lysate from step (ii) with a bioluminescent reporter bacteria incorporating a gene coding for a deoxyribonucleoside kinase, a deoxyribonucleoside kinase transcription promoter and a dephosphorylating agent;
  (v) optionally, mixing a portion of the cell lysate from step (ii) with a bioluminescent reporter bacteria incorporating a gene coding for deoxyribonucleoside kinase; and
  (vi) measuring the bioluminescence of each of the mixtures from steps (iii), (iv) and optionally (v), wherein the comparative levels of bioluminescence of each of the mixtures provides a measure of the resistance or sensitivity to the drug.

According to a second aspect of the invention, a kit for determining the resistance or sensitivity of a cell line or patient sample to a deoxyribonucleoside kinase-dependant drug comprises a bioluminescent reporter bacteria incorporating a gene coding for a deoxyribonucleoside kinase, a deoxyribonucleoside kinase transcription promoter, and a dephosphorylating agent.

According to a third aspect of the invention, there is the use, ex vivo, of a dephosphorylating agent, a deoxyribonucleoside kinase transcription promoter, and a bioluminescent reporter incorporating a deoxyribonucleoside kinase gene for determining the resistance or sensitivity of a cell line or patient sample to a drug able to undergo phosphorylation by a deoxyribonucleoside kinase.

DESCRIPTION OF THE DRAWINGS

This invention is described with reference to the accompanying drawings, wherein.

DETAILED DESCRIPTION OF THE INVENTION

Figure 1:
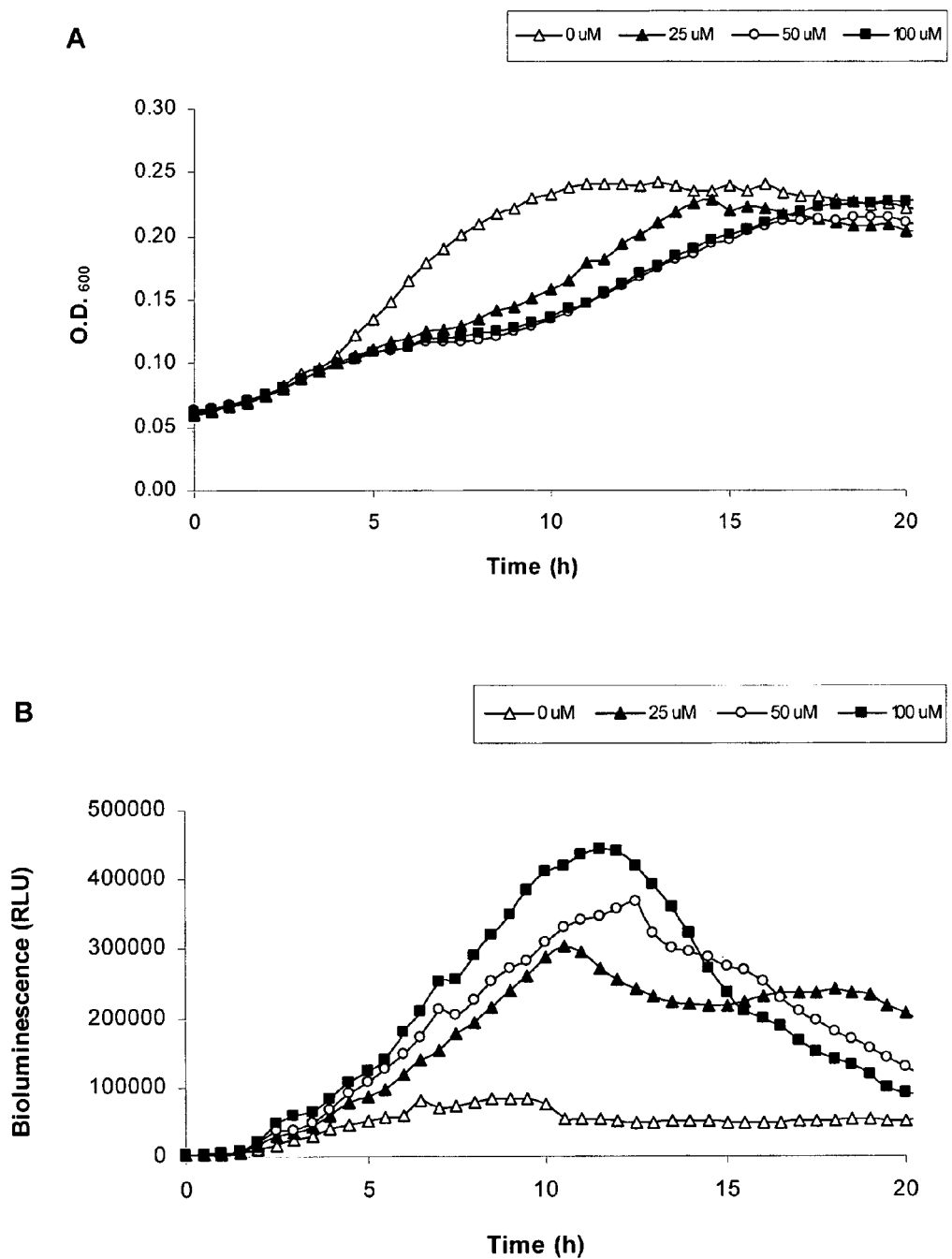
FIG. 1 shows graphs illustrating the response of the bioluminescent bacterial biosensor to Ara-C; graph (A) corresponds to growth measured using $OD_{600}$, and graph (B) corresponds to luminescence of the same cultures measured in Relative Light Units (RLU)

The present invention provides a method for rapidly determining the resistance or sensitivity of a patient cell sample or cell line to anti-cancer and anti-viral drugs. The method makes use of bioluminescent reporter bacteria with sensitivity to nucleoside analogue (NA) drugs which are dependant upon a deoxyribonucleoside kinase (dNK) for intracellular phosphorylation.

The invention relates to a cell lyate assay, which uses a bioluminescent bacteria as a reporter of drug activity and has considerable potential for use in the screening of virally-infected and cancerous cell sensitivity to dNK phosphorylation-dependent NA drugs. The assay is suitable for use in pre-screening of clinical samples prior to commencement of drug treatment and as an indicator of the efficacy of reduced dose therapy. Furthermore, the assay can be repeated at relapse in cancer patients in order to determine whether tumours have undergone clonal evolution and whether the drug could be used to achieve a second complete remission.

According to an embodiment of the present invention, bioluminescent reporter bacteria are mixed with drug-treated cell lysate and the bioluminescence emitted by the bacteria is measured in order to determine the sensitivity of the cells to the drug. Deoxycytidine deaminase (cdd)-deficient bacteria are sensitive to nucleoside analogue drugs and exhibit increased bioluminescence in their presence.

As used herein, the term 'bioluminescence' refers to the production of visible light in living organisms due to the oxidation of organic compounds (luciferins), in the presence of molecular oxygen ($O_2$) and energy (NADH), catalysed by the enzyme luciferase. The ability to emit light is dependent on the reducing power of the organism, hence only metabolically active bacteria can produce light.

The bioluminescence phenotype may be endogenous, or alternatively can be conferred upon most bacteria, for example by introducing and expressing the luxCDABE operon, isolated from *Photorhabdus luminescens*, under the control of constitutive promoters. Bioluminescent bacteria do not require exogenous substrate and emit light as a direct indicator of the physiological status of the bacteria in real time.

Intracellular concentrations of NA drugs lower than 0.05 μm can be detected by a surprising increase in light output from bioluminescent bacteria, and the technology is suitable for quantifying the response to the clinical NA dose ranges in 8 hours or less.

The bacteria of the invention may be any bacteria which is sensitive to NA drugs and expresses endogenous or exogenous genes which confer the bioluminescent phenotype. In a preferred embodiment, the bacteria is not capable of deaminating cytosine to uracil, and in a more preferred embodiment, does not express the enzyme deoxycytidine deaminase (cdd). The bacteria is preferably *E. coli*, more preferably *E. coli* MG 1655. MG 1655 is a derivative of wild-type *E. coli* K-12. Wild-type MG 1655 expresses deoxycytidine deaminase. Therefore, it is most preferable for the bacteria of the invention to be a deoxycytidine deaminase (cdd)-deficient strain of *E. coli* MG 1655. This strain is deposited as NCTC Accession No. 13427.

The method of the invention is carried out in vitro, i.e. outside of the body of the patient.

As used herein, the term "patient cell sample" refers to cells isolated from a patient. The cells of the cell sample will typically be cancerous or virally-infected cells, e.g. acute myeloid leukaemic cells.

The term "patient" refers to a mammal including a non-primate (e.g. a cow, pig, horse, cat, dog, rat and mouse) and a primate (e.g. a monkey and a human), and more preferably a human.

In a preferred embodiment, the sample material is bone marrow or white blood cells obtained from peripheral blood, for example by using standard phlebotomy techniques.

The term "cell line" refers to an immortalised ex vivo cell culture. The cells of the cell line will typically be cancerous or virally-infected cells, e.g. acute myeloid leukaemic cells.

The term 'untreated control cell' refers to cells of the patient cell sample or cell line which have not been treated with a deoxyribonucleoside kinase-dependent drug.

The methods and kits of the invention can be used to determine resistance or sensitivity to deoxyribonucleoside kinase-dependent drugs, i.e. NA drugs that utilise a deoxyribonucleoside kinase (dNK) pathway. Table 1 provides a non-exhaustive list of examples of anti-viral and anti-cancer drugs whose mechanism of action is dependent upon phosphorylation by dNK.

TABLE 1

| Drug | dNK Enzyme | Clinical Use |
| --- | --- | --- |
| Cladribine | dCK, dGK | Hairy cell leukaemia, Multiple Sclerosis |
| Fludarabine | dCK | Leukaemia |
| Ara-C | dCK | AML |
| Gemcitabine | dCK, TK2 | Pancreatic, breast and non-small cell lung cancers |
| Nelarabine | dGK, dCK | T-cell acute lymphoblastic leukaemia |
| Clofarabine | dCK | Leukaemia |
| Troxacitabine | dCK | AML |
| Zalcitabine | dCK | HIV |
| Lamivudine | dCK | HIV |
| Zidovudine | TK2 | HIV |
| Stavudine | TK1 | HIV |
| Acyclovir | TK | Herpes virus |

The term 'deoxyribonucleoside kinase-dependent drugs' refers to nucleoside analogue drugs whose mechanism of action is dependent upon intracellular phosphorylation at the 5' position by a deoxyribonucleoside kinase. The deoxyribonucleoside kinase can be thymidine kinase 1 or 2 (TK1 and TK2), deoxycytidine kinase (dCK) or deoxyguanosine kinase (dGK). Preferably, the deoxyribonucleoside kinase is deoxycytidine kinase.

The deoxyribonucleoside kinase-dependent drug of the invention may be a DNA-disrupting drug, i.e. a drug that prevents cellular DNA replication by direct interference with cellular DNA through incorporation into or modification of said DNA, or by indirect interference through incorporation into or modification of DNA-replicating enzymes such as DNA polymerase.

In a preferred embodiment of the invention, the deoxyribonucleoside kinase-dependent drug is a member of a structural class comprising purine (adenine and guanine) or pyrimidine (cytosine, thymine and uracil) nucleoside groups. Preferably, the drug is an anti-cancer drug or an anti-viral drug. More preferably, the drug is selected from the list of drugs in Table 1, and most preferably the drug is Ara-C or fludarabine.

The term 'drug resistance' is defined herein as the inability of a mammalian cell to interact with a drug in the same way that a normal or non-resistant cell would, which results in the failure of the drug to achieve the desired effect. The term 'drug sensitivity' refers to the ability of a cell to interact with a drug, wherein the cell is not resistant to the drug.

In its broadest aspect, the method of the invention comprises carrying out at least two, optionally three, assays which produce two (optionally three) bioluminescence readings that are used to determine the resistance or sensitivity of a cell sample to NA drugs. According to this method, one or more cell lines or patient cell samples are isolated and either the entire sample or a portion thereof is treated with a deoxyribonucleoside kinase-dependent drug. The treated cells are then lysed and the cell lysate is split into two (optionally three) samples. The first sample is added to a bioluminescent reporter bacteria incorporating a gene coding for a deoxyribonucleoside kinase, in the presence of a deoxyribonucleoside kinase transcription promoter. This mixture is termed "LI". The second sample is added to a bioluminescent reporter bacteria incorporating a gene coding for a deoxyribonucleoside kinase, in the presence of a deoxyribonucleoside kinase transcription promoter and also a dephosphorylating agent. This mixture is termed "LIP". The optional third sample is added to a bioluminescent reporter bacteria. The promoter and dephosphorylating agent are not present in the mixture. This assay enables the discrimination of a patient who does not metabolise the drug and a patient who does not take up the drug and is termed "L". It is preferable that the method is carried out with the third assay as this allows a test for partial metabolism of the drug. If only the first two assays are carried out, this will test for total or substantial resistance.

A particular advantage of the methods of the invention is the use of the assay with the dephosphorylating agent, i.e. the second assay "LIP". This provides an internal reference with which the sensitivity/resistance of the patient sample/cell line to the drug can be measured.

Deoxyribonucleoside kinases phosphorylate deoxyribonucleosides at the 5' position. The deoxyribonucleoside kinase coded for by a gene incorporated into the bioluminescent reporter bacteria can be thymidine kinase 1 or 2 (TK1 and TK2), deoxycytidine kinase (dCK) or deoxyguanosine kinase (dGK) and is a preferably mammalian deoxyribonucleoside kinase. More preferably, the deoxyribonucleoside kinase is deoxycytidine kinase. Most preferably, the deoxycytidine kinase is human deoxycytidine kinase.

As used herein, the term 'deoxyribonucleoside kinase transcription promoter' refers to any agent capable of initiating the process of expression of the deoxyribonucleoside kinase gene. The promoter/agent may induce the expression of the kinase gene by acting on the regulatory elements of the gene. Many such "inducers" are known in the art. In a preferred embodiment of the invention, the deoxyribonucleoside kinase transcription promoter is isopropyl β-D-1-thiogalactopyranoside (IPTG). IPTG is identified herein as a molecule with the molecular formula $C_9H_{18}O_5S$ and the CAS registry number 367-93-1.

As used herein, the term 'dephosphorylating agent' refers to any agent capable of removing phosphate groups from nucleotides. In a preferred embodiment of the invention, the dephosphorylating agent is an alkaline phosphatase, which is a hydrolyase enzyme identified herein as EC 3.1.3.1. Suitable alkaline phosphatases include bacterial alkaline phosphatase (BAP), calf intestinal alkaline phosphatase (CTAP), shrimp alkaline phosphatase (SAP) and bovine intestinal mucosa alkaline phosphatase (BIMAP).

According to the method described above, resistance or sensitivity of cells to the nucleoside analogue drug is determined by measuring and comparing the bioluminescence of the cell lysate mixtures from each of the bioluminescent reporter bacteria assays. The bacteria of the invention are sensitive to activated (triphosphorylated) nucleoside analogue drugs. The drug enters the reporter bacteria in its inactive, unphosphorylated form and is then phosphorylated intracellularly by dNKs expressed by the bacteria under the influence of an inducible transcription promoter in order to cause an increase in bacterial bioluminescence.

In another embodiment, the method of the invention comprises six assays. The first three assays correspond to the drug-treated assay samples described above. The second three assays comprise untreated blank controls which do not contain any drug. These assay samples are produced by subjecting untreated cells from the patient sample or cell line to lysis, dividing the lysed cells into three samples and then adding the portioned samples to (i) a bioluminescent reporter bacteria (L), (ii) a bioluminescent reporter bacteria incorporating a gene coding for a deoxyribonucleoside kinase, in the presence of a deoxyribonucleoside kinase transcription promoter (LI), and (iii) a bioluminescent reporter bacteria incorporating a gene coding for a deoxyribonucleoside kinase, in the presence of a deoxyribonucleoside kinase transcription prompter and a dephosphorylating agent (LIP) respectively. The bioluminescence of each of the three assays is measured and the value of each is subtracted from the bioluminescence value measured for the corresponding drug-treated assay. The resulting value is then used to determine the resistance or sensitivity of cells to the drug.

The six assay method is beneficial since it allows background luminescence to be subtracted from the bioluminescence measurement of the assay mixture and therefore provides a more accurate value for use in determining cellular resistance or sensitivity. Although the impact of the deoxyribonucleoside kinase transcription promoter (e.g. IPTG) and dephosphorylating agent (e.g. BAP) on bioluminescent output may be minimal, their effect can be determined by measuring and comparing the bioluminescent output of the LIP assay of the drug-treated patient samples or cell lines with the LIP assay of the untreated patient samples or cell lines.

This method can also be carried out as a four assay method, if the optional third assay (L) is not carried out. The result is useful in predicting total or substantial resistance to the drug.

In a preferred embodiment, when all three assays are carried out, cell samples are categorised according to one of four possible interactions with drug: drug taken up by the cell and metabolised; drug taken up by the cell and partially metabolised; drug taken up by the cell but not metabolised; and drug not taken up by the cell. The schematic of FIG. 4 and the graphs of FIG. 5 outline this. The control (L) is necessary to discriminate between full drug metabolism and partial drug metabolism, as well as to discriminate between the two modes of resistance, lack of take up or lack of intracellular phosphorylation.

If the treated cells do not take up the drug, there will be no drug present in the cell lysate. The measurements for each of the bioluminescent reporter assays will be similar, and there will be no significant drug-induced increases in bioluminescence when compared with the corresponding controls, indicating that the cells are resistant to the drug.

If the treated cells take up but do not metabolise the drug, following drug administration and cell lysation there will be only unphosphorylated drug present, which results in the bioluminescent reporter bacteria taking up the unphosphorylated drug regardless of the presence or absence of alkaline phosphatase. Therefore, in both LIP and LI assays, light output will be approximately equal and significantly greater than for the control assay (L).

If the treated cells take up and partially metabolise the drug, following drug administration and cell lysation, there will exist phosphorylated and unphosphorylated drug. In the LI assay, the bioluminescent reporter bacteria can only take up the unphosphorylated drug and not the phosphorylated drug, resulting in a reduced light output compared to the LIP assay which takes up all the drug due to the presence of the dephosphorylating agent. The measured bioluminescence of the LI assay will be significantly less than that of the LIP assay but significantly greater than the control assay (L).

If the treated cells take up and metabolise the drug, following drug administration and cell lysation, all the added drug will be phosphorylated. In the LI assay, the bioluminescent reporter bacteria cannot take up the phosphorylated drug, resulting in a measured bioluminescence similar to the control assay (L) but significantly lower than the LIP assay, in which all of the drug is taken up.

Bioluminescence is measured in Relative Light Units (RLU). This can be achieved using a range of techniques known in the art, including multimode microplate readers, light sensitive CCD cameras, single tube luminometers and light sensitive paper (including photographic film).

The present invention relates to methods and kits for deriving the RLU data, however there are several different ways in which the RLU data could be computed to determine the nature of the interaction between the drug and the cell line or patient cell sample.

The following general formulae can be applied to determine which category applies to a given cell sample:

when the measured bioluminescence values for each assay sample are such that LIP>LI and LIP>L and LI≈L, the cells are said to be sensitive, i.e. take up and metabolise the drug;

when the measured bioluminescence values for each assay sample are such that LIP>L and LI>L and LIP≈LI, the drug is taken up but not metabolised;

when the measured bioluminescence values for each assay sample are such that LIP>LI>L, the drug is taken up and partially metabolised; and when the measured bioluminescence values for each assay sample are such that LIP≈LI≈L, the drug is not taken up, wherein L=lysate and a bioluminescent reporter bacteria, LI=lysate and a bioluminescent reporter bacteria incorporating a gene coding for a deoxyribonucleoside kinase and a kinase transcription promoter, LIP=lysate and a bioluminescent reporter bacteria incorporating a gene coding for a deoxyribonucleoside kinase and a kinase transcription promoter and a phosphatase.

The symbol "≈" indicates that values are approximately equal, since the deoxyribonucleoside kinase transcription promoter may cause slight alterations to light output which means that essentially equivalent values are not exactly equal.

In further embodiments of the invention, the following formulae are used in order to determine which category applies to a given cell sample. If the three assay method is used, the formula is as follows:

$$\% \text{ Int} = [T(n/m)] \times 100$$

where % Int=% interaction, T=treatment (drug) and:
n=LIP and m=LI; or
n=LIP and m=L; or
n=LI and m=L.
wherein:
the patient sample or cell line takes up and metabolise the deoxyribonucleoside kinase-dependent drug if % Int=>10% when n=LIP, m=LI and % Int<10% when n=LI, m=L the patient sample or cell line takes up and does not metabolise the deoxyribonucleoside kinase-dependent drug if % Int=<10% when n=LIP, m=LI and % Int>10% when both n=LI, m=L, and n=LIP, m=L the patient sample or cell line takes up partially metabolises the deoxyribonucleoside kinase-dependent drug if % Int=>10% when n=LIP, m=LI and % Int>10% when n=LI, m=L the patient sample or cell line does not takes up the deoxyribonucleoside kinase-dependent drug if % Int=<10% when n=LIP, m=LI and n=LI, m=L and n=LIP, m=L If the six assay method incorporating the blank control assays is used, the formula is as follows:

$$\% \text{ Int} = [(Tn/Tm) - (Cn/Cm)] \times 100$$

wherein:
% Int=% interaction; T=treatment (drug); C=control (no drug) and:
n=LIP and m=LI; or
n=LIP and m=L; or
n=LI and m=L.
wherein:
the patient sample or cell line takes up and metabolises the DNA-disrupting deoxyribonucleoside kinase-dependent drug if % Int=>10% when n=LIP, m=LI and % Int<10% when n=LI, m=L;

the patient sample or cell line takes up and does not metabolise the DNA-disrupting deoxyribonucleoside kinase-dependent drug if % Int=<10% when n=LIP, m=LI and % Int>10% when both n=LI, m=L, and n=LIP, m=L;

the patient sample or cell line takes up and partially metabolises the DNA-disrupting deoxyribonucleoside kinase-dependent drug if % Int=>10% when n=LIP, m=LI and % Int>10% when n=LI, m=L;

the patient sample or cell line does not take up the DNA-disrupting deoxyribonucleoside kinase-dependent drug if % Int=<10% when n=LIP, m=LI and n=LI, m=L and n=LIP, m=L.

In a further embodiment of the invention, for the assessment of drug sensitivity in a patient cell sample or cell line, the above-described formulae can have the following cut-off values:

the patient sample or cell line takes up and metabolises the deoxyribonucleoside kinase-dependent drug if % Int=>5% when n=LIP, m=LI and % Int=<10% when n=LI, m=L the patient sample or cell line takes up and does not metabolise the deoxyribonucleoside kinase-dependent drug if % Int=<10% when n=LIP, m=LI and % Int>5% when both n=LI, m=L, and n=LIP, m-L the patient sample or cell line takes up and partially metabolises the deoxyribonucleoside kinase-dependent drug if % Int=>5% when n=LIP, m=LI and % Int>5% when n=LI, m=L the patient sample or cell line does not takes up the deoxyribonucleoside kinase-dependent drug if Int=<10% when n=LIP, m=LI and n=LI, m=L and n=LIP, m=L As used herein, the term 'taken up' refers to the drug being absorbed by the cell from the extracellular space into the cytosol.

The term 'metabolise' refers to structural modification of a molecule by an organism.

As used herein, a drug that is said to be 'metabolised' has been phosphorylated, therefore the LI and L assay curves are close to parity and have a markedly lower light output than the LIP assay curve.

A drug that is said to 'not be metabolised' is substantially or fully unaltered structurally and is unphosphorylated, therefore the LIP and LI assay curves are close to parity and have a markedly greater light output than the lysate treatment.

A drug is said to be 'partially metabolised' if the ratio of unaltered parent drug to phosphorylated parent drug resides in the region between that of a fully metabolised and fully-non-metabolised drug, therefore the light output of the LI assay is markedly less than the LIP assay but markedly greater than the light output of the L assay.

As mentioned above, the method of the invention can be carried out with only the first two assays being performed. In this case, the values will be LI and LIP (the value L is not obtained). The resistance of a cell line or a patient sample can be categorised as follows:

when bioluminescence of LIP≈LI, the patient sample or cell line is resistant to the drug (totally or substantially resistant).

The resistance can be categorised by applying the following formula:

$$\% \text{ Int}=[T(n/m)]\times 100$$

where n=LIP and m=LI, and wherein the patient sample or cell line is substantially resistant to the drug if % Int=<10%.

If the four assay method is used, incorporating the blank control assays, resistance is categorised by the following formula:

when bioluminescence of $$[T(n)-C(n)]\approx[T(m)-C(m)]$$

there is resistance to the drug.
The definitions for the formulae are the same as before.
The formula may also be expressed as:

$$\% \text{ Int}=[T(n/m)-C(n/m)]\times 100$$

wherein n=LIP and m=LI, and
wherein there is substantial resistance if
% Int=<10%
The definitions for the formula are the same as before.

In another embodiment, the present invention provides a kit suitable for use in determining the sensitivity of a cell line or patient cell sample to a deoxyribonucleoside kinase-dependant drug. The kit comprises a bioluminescent reporter bacteria incorporating a gene coding for a deoxyribonucleoside kinase, a deoxyribonucleoside kinase transcription promoter, and a dephosphorylating agent.

The invention will now be described by reference to the following non-limiting example.

Method

Bacterial Strains, Plasmids and Growth Media. *E. coli* SØ5218 is a cdd-deficient strain expressing the human dCK cDNA on the IPTG-inducible pTrc99-A plasmid. *E. coli* MG1655 is a derivative of the wild-type *E. coli* K-12 with a requirement for pyrimidine in minimal medium, due to suboptimal expression of the orotate phosphoribosyltransferase gene coded for by pyrE. Both strains were made self-bioluminescent by transforming them with the broad-host vector pBBR1MCS-2 carrying the luxCDABE cassette from *Photorhabdus luminescens* as an EcoRI PCR fragment. Luria-Bertani (LB) medium was used for routine culturing of bacteria. The antibiotics ampicillin (to maintain pTrc-A) and kanamycin (to maintain pBBR1MCS-2) were added at 100 and 10 µg/ml, respectively. Growth inhibition experiments were performed in LB RPMI 1640 or in minimal salt medium (AB) plus 0.2% glucose, 0.2% vitamin-free casamino acids and supplemented with thiamine and leucine.

Cell lines, bone marrow and blood samples. The monocytic cell line KG-1a (DSMZ, Germany) was grown and maintained as a cell suspension in RPMI 1640 medium supplemented with 2 mM L-glutamine and 10% foetal calf serum. Mononuclear cell fractions were isolated from patient peripheral blood or bone marrow samples (n=8) using density gradient centrifugation (SG 1.007) followed by resuspension in RPMI 1640 medium prior to incubation with Ara-C. Cryopreserved bone marrow samples were thawed and re-suspended in RPMI 1640 medium prior to drug exposure. In all cases leukaemic samples had a blast burden >80%.

Construction of a cdd-deficient strain of *E. coli* MG 1655. A library of *E. coli* MG 1655 strains was constructed using transposition mutagenesis with P1 phage carrying the Tn10 transposon. Mutants carrying the transposon were selected for by plating on tetracycline (10 µg/ml) agar plates and cdd mutants were selected for by plating on to plates containing 10 µg/ml of the analogue 5-fluoro-2' deoxycytidine which is toxic to *E. coli* expressing cdd. The phenotype of cdd mutants was confirmed by the absence of cytidine deaminase activity.

Cell Lysis Assay. AML cell lines or patient derived samples were treated with 25 µM Ara-C for 90 min at 37° C. and 5% $CO_2$, harvested, washed and resuspended in fresh RPMI 1640 medium. EDTA and saponin were added to final concentrations of 1.5 mM and 0.1%, respectively. Samples were then vortexed for 30 sec and cell debris were removed by centrifugation at 1027 g for 5 min. Samples from the lysate or supernatant were mixed with reporter bacteria, 1 mM of IPTG an 10 units of alkaline phosphatase. Bioluminescence and growth ($OD_{600}$) of the bacteria were monitored in a multimode microplate reader. Sensitivity of AML cell lines or patient derived samples to Ara-C was also assayed using Cell Titer-Glo® Luminescent Cell Viability Assay kit (Promega). Samples were treated with 25 µM Ara-C for 72 hours at 37° C. and 5% $CO_2$ before measuring intracellular levels of ATP according to manufacturer's instructions. Paired t-tests were used to analyse significant differences in bioluminescence output between control and treated assay samples.

Results

Ara-C has no effect on *E. coli* as it lacks deoxycytidine kinase (dCK) and deaminates Ara-C into Ara-uracil through the activity of deoxycytidine deaminase (cdd). The cdd-deficient E. coli mutant (SØ5218) which, upon the expression of human dCK gene, exhibited reduced relative growth in the presence of Ara-C in basic minimal medium did not respond to Ara-C when it was assayed in a rich growth medium (data not shown), due to competition of Cytosine Tri-Phosphate (CTP) in the medium, with Ara-CTP incorporation into bacterial DNA.

In order to measure Ara-C response in a nutrient rich intracellular environment, an alternative cdd-deficient strain of a bioluminescent E. coli MG1655 mutant was constructed using transposon mutagenesis, which was further transformed with pTrc99-A, to give IPTG inducible expression of dCK. The newly constructed reporter strain (NCTC 13427) showed reduced growth in the presence of Ara-C, when induced by IPTG, in nutrient rich medium. FIG. 1 shows the effect of Ara-C on the growth and bioluminescence output from the same bacterial cultures. Growth was decreased in drug treated cultures (FIG. 1A) but, unexpectedly, Ara-C caused a significant increase in light output ($p=0.0001$) from the same drug-treated cultures (FIG. 1B). These effects were only observed in the presence of IPTG, suggesting that the activity of human dCK results in incorporation of Ara-CTP into bacterial DNA. One possible explanation for the light increase is that the DNA damage caused by Ara-CTP induces bioluminescence that could be used in DNA repair by a photo-reactivation process.

Figure 2:
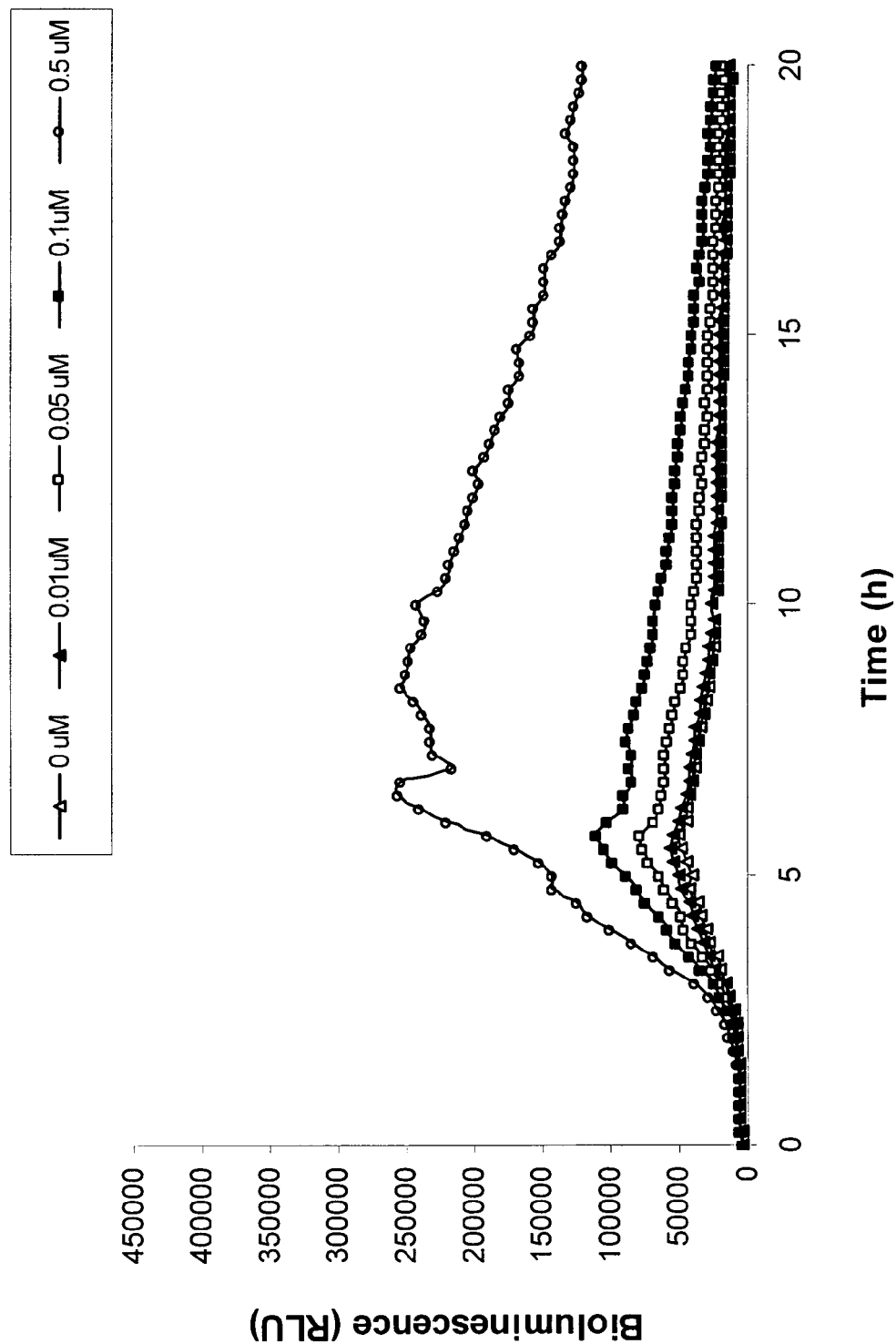
FIG. 2 is a graph illustrating bioluminescent biosensor response to low concentrations of Ara-C.

Experiments with NCTC 13427 (lux+cdd deficient E. coli MG 1655) with low concentrations of Ara-C (FIG. 2) indicated that the bacterial biosensor is highly sensitive and responds to Ara-C concentrations as low as 0.05 µM.

Figure 3:
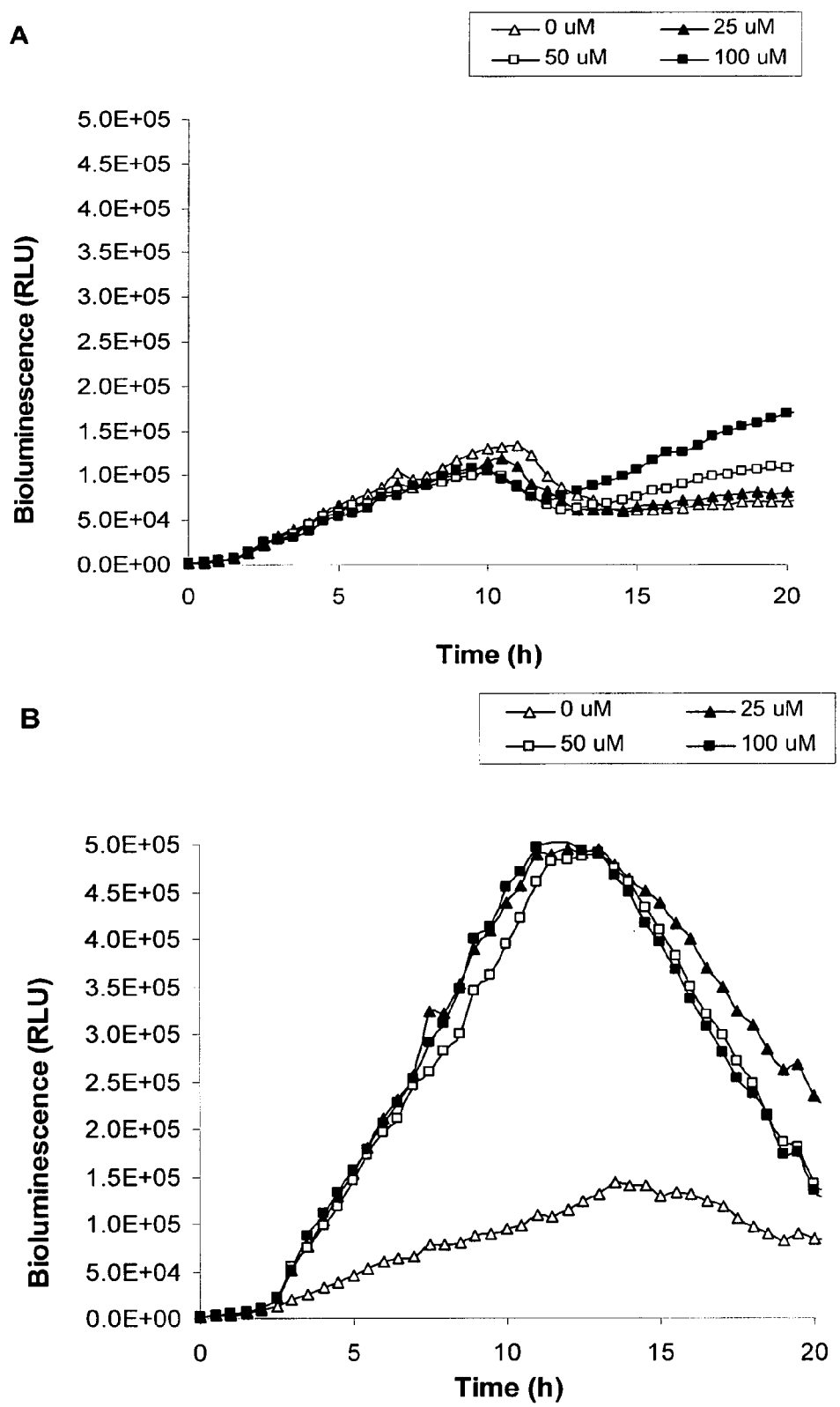
FIG. 3 shows graphs illustrating biosensor responses to Ara-CTP. Graph (A) corresponds to the response of the bacterial biosensor to Ara-CTP added at different concentrations. Graph (B) corresponds to the response of the bacterial biosensor when BAP is added to the assay at the start, followed by Ara-CTP at different concentrations.

In order to increase the specificity of the proposed assay, direct effects of the active intracellular drug derivative, Ara-CTP, on the bacterial biosensor were monitored (FIG. 3A). Results indicate that Ara-CTP does not directly enter reporter bacteria. The increase in light output observed after at least 15 h of growth could be due to bacterial production of alkaline phosphatase (known to be up-regulated during E. coli stationary phase) dephosphorylating Ara-CTP, that can then enter reporter bacteria. To verify this, the assay was repeated with the addition of alkaline phosphatase at the start. This resulted in an increase in light output which was evident after 3-5 hours, similar to that observed with Ara-C (FIG. 3B).

By measuring bioluminescence increase in the presence and absence of alkaline phosphatase (+/−), it was possible to quantify the intracellular conversion of Ara-C to its active metabolite, within leukaemic cells.

Figure 4:
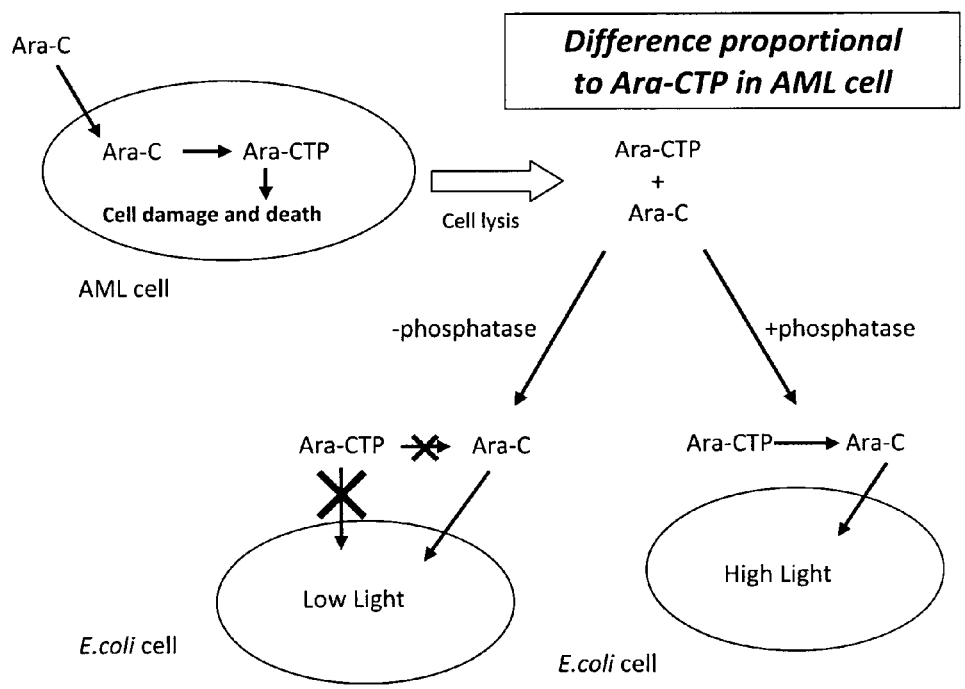
FIG. 4 is a schematic illustration of the cell lysis assay using a bioluminescent bacterial biosensor to show intracellular response to Ara-C.
Figure 5:
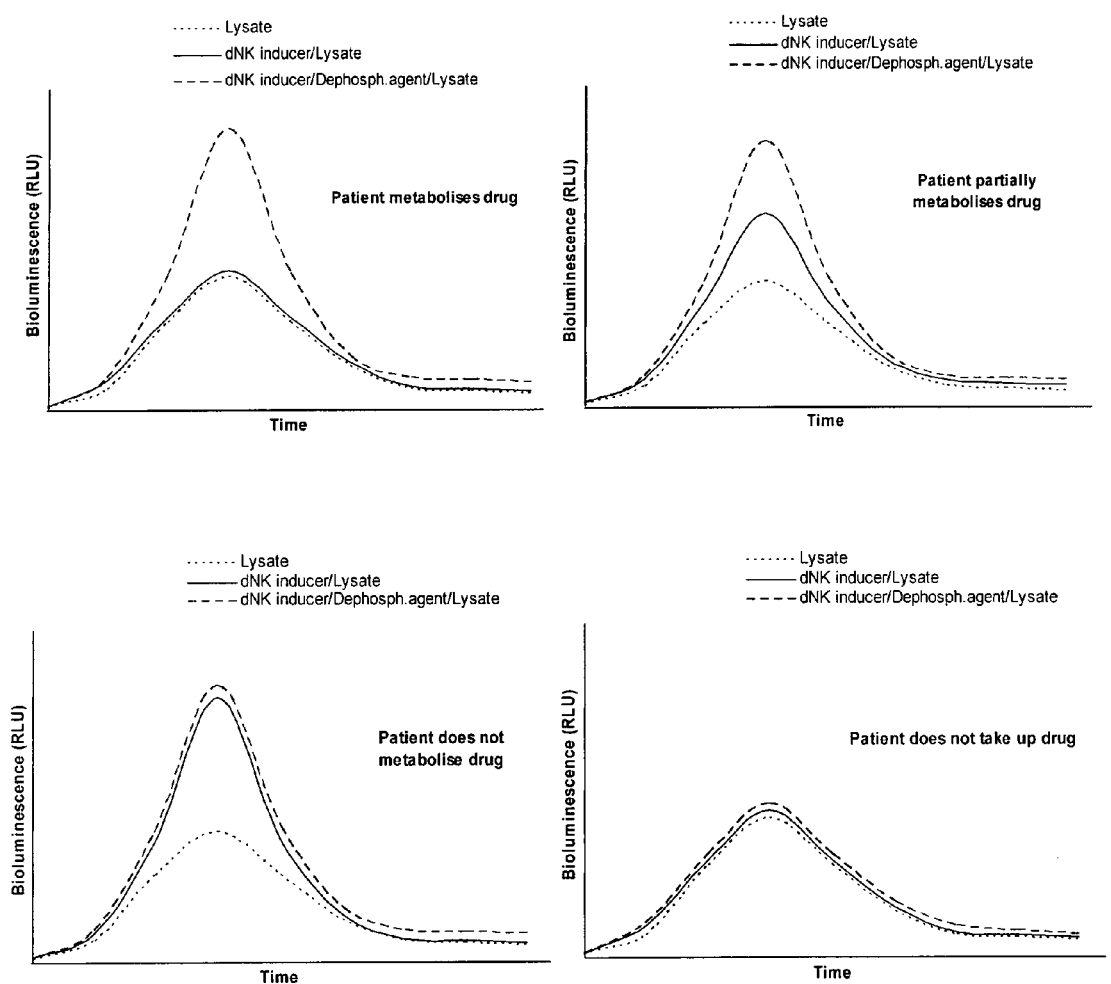
FIG. 5 shows four graphs illustrating the four treatment response profiles.

Running the +/−phosphatase assay in parallel with the 90 minute lysis protocol enabled determination of the proportion of Ara-C to Ara-CTP conversion within AML cells via comparison of light output from the phosphatase −ve assay (unconverted/inactive Ara-C 'detected') and from the phosphatase +ve assay (all intracellular Ara-C 'detected'). A schematic of this protocol is shown in FIG. 4. A representation of light output during the bioluminescent assay for patients who are metabolic sensitive, metabolic resistant, metabolic partially resistant and uptake resistant is shown in FIG. 5.

Figure 6:
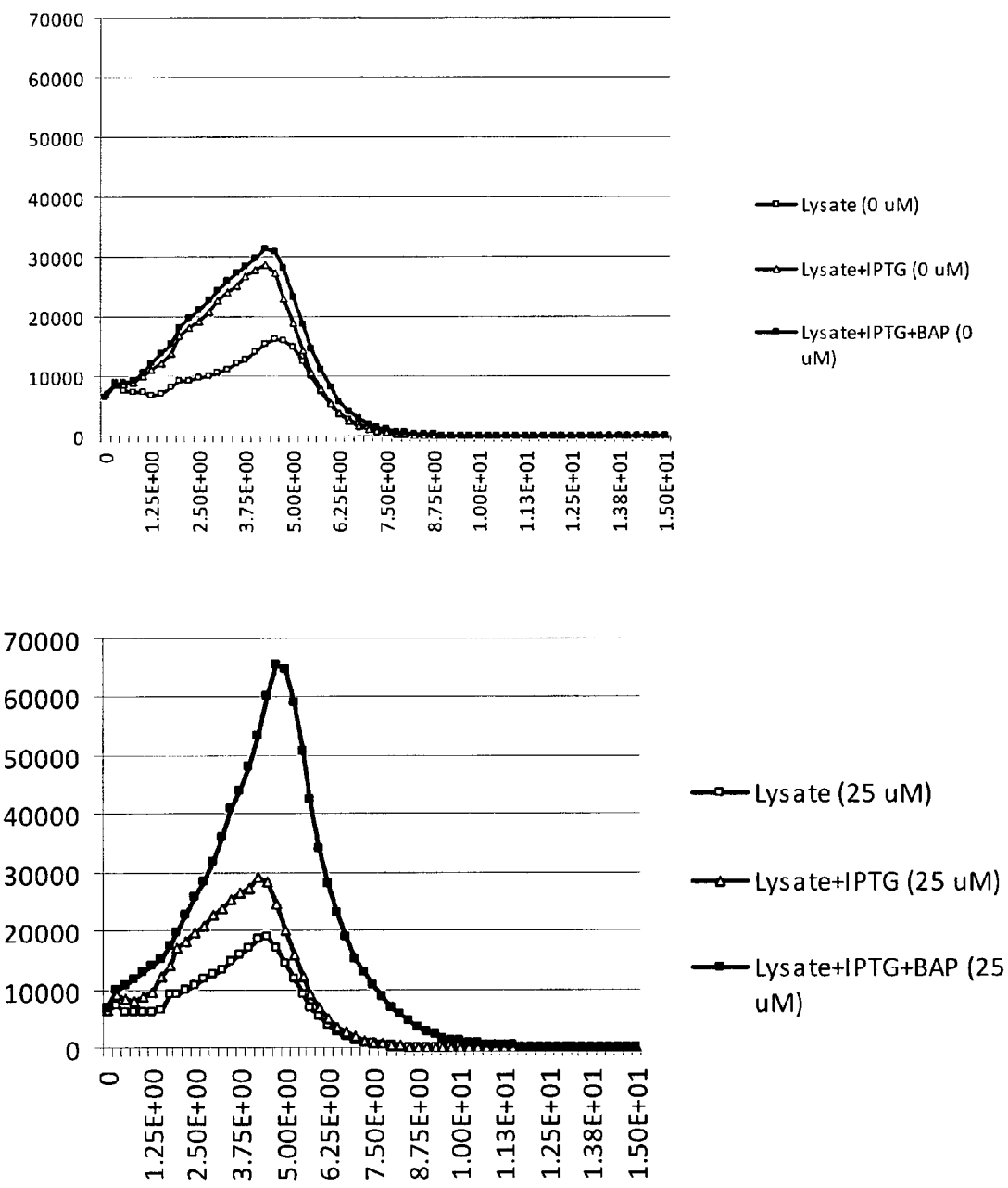
FIG. 6 illustrates the response of Ara-C sensitive KG1-a cells to 25 μM Ara-C and to a control.

The assay was evaluated using a KG-1a cell line and AML samples from patients with known response to Ara-C used in induction therapy. FIG. 6 depicts the light output from the lysate of the Ara-C sensitive cell line KG-1a treated with high (25 µM) Ara-C concentrations. Results clearly show a significant increase in the light output from the IPTG-induced lysate, with ($p=0.0001$) and without ($p=0.0001$) BAP indicating the presence of Ara-C and Ara-CTP within the leukaemic cells. The three day cytotoxicity test confirmed that KG-1a cells are sensitive to Ara-C.

Figure 7:
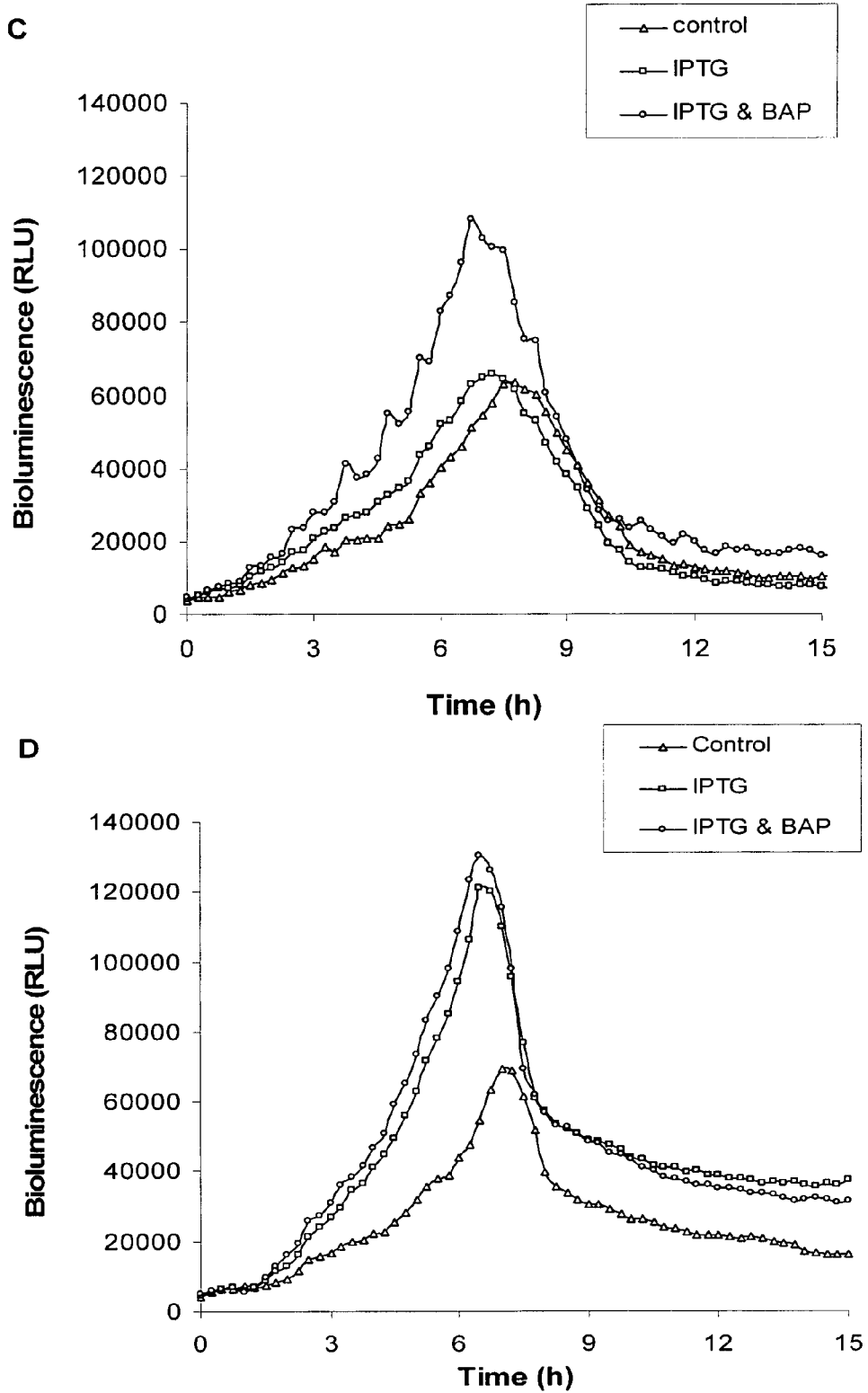
FIG. 7 shows two graphs illustrating the effect of 25 μM Ara-C on a peripheral blood sample from an Ara-C responsive AML patient (graph (C)) and a peripheral blood sample from an Ara-C resistant AML patient (graph (D)).

The cell lysis assay was applied to clinical samples of peripheral blood (n=5) from AML patients. Typical results for Ara-C sensitive and resistant patients are shown in FIGS. 7(C) and (D). A summary of data from 6 patients comparing the cytotox and bioluminescent assays is given in Table 2. These preliminary assays, conducted on 7 clinical samples, gave 100% correlation with clinical response to therapy.

TABLE 2

| Patient | Diagnosis | Clinical Outcome | Cytotox Assay (DLO) | Bioluminescent Assay (sensitive) |
|---|---|---|---|---|
| 1 | M2 | NR | 84% | No |
| 2 | M4 | CR | 99% | Yes |
| 3 | M2 | NR | 79% | No |
| 4 | M4 | CR | 99% | Yes |
| 5 | M4 | NR | 62% | No |
| 6 | M0 | NR | 5% | No |
| 7 | M3 | Remission death | 91% | No |

DLO = differential light output;
M0-M4 = AML classification;
NR = No remission;
CR = Complete remission Table 3 validates the application of the bioluminescent assay using relative percentage differences in peak light output from the various treatments to identify resistant and sensitive patients. Data shown in Table 3 is computed according to the equation $\{[\text{RLU drug treated sample (LIP/LI)} - \text{RLU control (LIP/LI)}] \times 100\}$, using c) as an example.

TABLE 3

| | Treatment % difference in peak RLU | | | Clinical |
|---|---|---|---|---|
| Patient | a) L:LI | b) L:LIP | c) LI:LIP | Outcome |
| 1 | −10.25 | 19.20 | 24.19 | sensitive |
| 2 | −4.00 | 62.40 | 48.03 | sensitive |
| 3 | −81.04 | −120.00 | −4.51 | resistant |
| 4 | 2.28 | 3.28 | 0.88 | unconfirmed |
| 5 | −61.46 | −98.39 | −13.87 | unconfirmed |
| 6 | −13.59 | −7.03 | 5.50 | unconfirmed |
| 7 | −16.37 | −16.37 | 1.20 | resistant |

L = lysate;
LI = lysate + dNK transcription promoter;
LIP = lysate + dNK transcription promoter + dephosphorylating agent As can be seen from Table 3, patients 1 and 2 take up and metabolise the drug, in which LIP has an obviously greater RLU % value than both LI and L, which in turn have similar values i.e. the top left-hand diagram of FIG. 5. Conversely, the profile of patient 3 is represented by the bottom left-hand diagram, suggesting the patient takes up but does not metabolise the drug. Patient 4, although not clinically confirmed, appears to be resistant to take up of the drug as the RLU % values for a), b) and c) are similar (bottom right-hand diagram of FIG. 5).

In conclusion, it is possible to determine the interaction of the drug with a patient sample or cell line.

The microorganism described herein as E. coli MG 1655 has been deposited under the terms of the Budapest Treaty on July 7, 2008, as NCTC 13427, National Collection of Type Cultures, Health Protection Agency, Centre for Infections, 61 Colindale Avenue, London NW9 5EQ, United Kingdom.

The invention claimed is:

1. A method for determining the resistance or sensitivity of a cell line or patient sample to a deoxyribonucleoside kinase-dependent drug, the method comprising the steps of:

(i) treating a patient sample or cell line, or a portion thereof, with a deoxyribonucleoside kinase-dependent drug;
(ii) lysing the cells of the patient sample or cell line from step (i);
(iii) mixing a portion (1) of the cell lysate from (ii) with (A) a bioluminescent reporter bacteria incorporating a gene coding for a deoxyribonucleoside kinase and (B) a deoxyribonucleoside kinase transcription promoter, wherein the mixture of (iii) does not include a dephosphorylating agent;
(iv) mixing a portion (2) of the cell lysate from step (ii) with (A) a bioluminescent reporter bacteria incorporating a gene coding for a deoxyribonucleoside kinase, (B) a deoxyribonucleoside kinase transcription promoter and (C) a dephosphorylating agent; and
(v) measuring the bioluminescence of each of the mixtures from steps (iii) and (iv); and
(vi) comparing the levels of bioluminescence of each of the mixtures from steps (iii) and (iv), wherein the comparative levels of bioluminescence of the two mixtures from steps (iii) and (iv) provide a measure of the resistance or sensitivity to the drug, wherein (A), (B) and (C) are three separate components.

2. The method of claim 1, further comprising the steps of:
(vii) mixing a portion of the cell lysate from step (ii) with a bioluminescent reporter bacteria incorporating a gene coding for deoxyribonucleoside kinase; and
(viii) measuring the bioluminescence of the mixture from step (vii),
wherein the comparative levels of bioluminescence of each of the mixtures from steps (iii), (iv) and (vii) provides a measure of the resistance or sensitivity to the drug.

3. The method of claim 1, further comprising the steps of:
a) subjecting untreated cells from the patient sample or cell line to lysis;
b) mixing a portion of the cell lysate from step (a) with a bioluminescent reporter bacteria incorporating a gene coding for a deoxyribonucleoside kinase and a deoxyribonucleoside kinase transcription promoter;
c) mixing a portion of the cell lysate from step (a) with a bioluminescent reporter bacteria incorporating a gene coding for a deoxyribonucleoside kinase and a deoxyribonucleoside kinase transcription promoter and a dephosphorylating agent; and
e) measuring the bioluminescence of each of the mixtures from steps (b) and (c) and subtracting each value from the corresponding bioluminescence value measured in steps (iii) and (iv), respectively, of claim 1,
wherein comparison of the resulting values for the bioluminescence of each assay provides a measure of resistance or sensitivity to the drug.

4. The method of claim 1, wherein the bioluminescent reporter bacteria is a deoxycytidine deaminase (cdd)-deficient strain of *E. coli* MG 1655.

5. The method of claim 1, wherein the bioluminescent reporter bacteria expresses the luxCDABE operon.

6. The method of claim 5, wherein the bioluminescent reporter bacteria is deposited as Accession No. NCTC 13427.

7. The method of claim 1, wherein the deoxyribonucleoside kinase is thymidine kinase 1, thymidine kinase 2, deoxycytidine kinase or deoxyguanosine kinase.

8. The method of claim 1, wherein the deoxyribonucleoside kinase is deoxycytidine kinase.

9. The method of claim 1, wherein the deoxyribonucleoside kinase transcription promoter is an IPTG inducible promoter.

10. The method of claim 1, wherein the dephosphorylating agent is an alkaline phosphatase.

11. The method of claim 10, wherein the dephosphorylating agent is bacterial alkaline phosphatase, calf intestinal alkaline phosphatase, shrimp alkaline phosphatase or bovine intestinal mucosa alkaline phosphatase.

12. The method of claim 1, wherein the deoxyribonucleoside kinase-dependent drug is an anti-cancer drug or an antiviral drug.

13. The method of claim 1, wherein the deoxyribonucleoside kinase-dependent drug is Ara-C or fludarabine.

14. The method of claim 1, wherein the cells of the cell line or patient sample are cancerous or virally-infected cells.

15. The method of claim 14, wherein the cells are acute myeloid leukaemic cells.

* * * * *